United States Patent
Olson

(10) Patent No.: US 8,328,829 B2
(45) Date of Patent: Dec. 11, 2012

(54) HIGH CAPACITY DEBULKING CATHETER WITH RAZOR EDGE CUTTING WINDOW

(75) Inventor: William John Olson, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 1341 days.

(21) Appl. No.: 11/934,670

(22) Filed: Nov. 2, 2007

(65) Prior Publication Data

US 2008/0065124 A1    Mar. 13, 2008

(51) Int. Cl.
*A61B 17/22*    (2006.01)
*A61D 1/02*    (2006.01)

(52) U.S. Cl. ............... 606/159; 623/8; 604/22; 604/27; 604/35

(58) Field of Classification Search ............ 606/159; 623/8; 604/22, 27, 35
See application file for complete search history.

(56) References Cited

U.S. PATENT DOCUMENTS

| | | |
|---|---|---|
| 1,481,078 A | 1/1924 | Albertson |
| 2,178,790 A | 11/1939 | Henry |
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |

(Continued)

FOREIGN PATENT DOCUMENTS

CA    2000621    4/1990

(Continued)

OTHER PUBLICATIONS

Abstract of DE 44 44 166 A1 (1 page).

(Continued)

*Primary Examiner* — Gary Jackson
*Assistant Examiner* — Kevin Everage
(74) *Attorney, Agent, or Firm* — Alana T. Bergman, Esq.

(57) ABSTRACT

The present invention is an atherectomy catheter with a hollow head. The head has a window with at least one internal bladed edge, a plunger, and an adjustable angle nose. The angle of the nose can be manipulated by the operator to apply pressure to an artery wall, thereby forcing the window and the window cutting edge up against a plaque target on the opposite side of the artery wall. The position of the plunger can be manipulated by the operator to open or close the window, thereby exposing or not exposing the bladed window edge, and optionally also pinching off dangling plaque fragments. Cut plaque enters the hollow catheter head through the open window, and is stored inside the catheter for removal from the body and subsequent analysis. In some embodiments, the catheter head may have optional sensors, or the plunger may also serve as a rotary cutter.

27 Claims, 5 Drawing Sheets

U.S. PATENT DOCUMENTS

| | | |
|---|---|---|
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMichael et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinksi et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |

| Patent No. | Date | Inventor(s) |
|---|---|---|
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A * | 5/1997 | Farley et al. ................ 606/159 |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |

| | | | |
|---|---|---|---|
| 5,823,971 A | 10/1998 | Robinson et al. | |
| 5,824,039 A | 10/1998 | Piplani et al. | |
| 5,824,055 A | 10/1998 | Spiridigliozzi et al. | |
| 5,827,201 A | 10/1998 | Samson et al. | |
| 5,827,229 A | 10/1998 | Auth et al. | |
| 5,827,304 A | 10/1998 | Hart | |
| 5,827,322 A | 10/1998 | Williams | |
| 5,830,224 A | 11/1998 | Cohn et al. | |
| 5,836,957 A | 11/1998 | Schulz et al. | |
| 5,843,022 A | 12/1998 | Willard et al. | |
| 5,843,103 A | 12/1998 | Wulfman | |
| 5,843,161 A | 12/1998 | Solovay | |
| 5,855,563 A | 1/1999 | Kaplan et al. | |
| 5,865,748 A | 2/1999 | Co et al. | |
| 5,868,685 A | 2/1999 | Powell et al. | |
| 5,868,767 A | 2/1999 | Farley et al. | |
| 5,871,536 A | 2/1999 | Lazarus | |
| 5,873,882 A | 2/1999 | Straub et al. | |
| 5,876,414 A | 3/1999 | Straub | |
| 5,879,397 A | 3/1999 | Kalberer et al. | |
| 5,883,458 A | 3/1999 | Sumita et al. | |
| 5,888,201 A | 3/1999 | Stinson et al. | |
| 5,895,399 A | 4/1999 | Barbut et al. | |
| 5,895,402 A | 4/1999 | Hundertmark et al. | |
| 5,902,245 A | 5/1999 | Yock | |
| 5,910,150 A | 6/1999 | Saadat | |
| 5,911,734 A | 6/1999 | Tsugita et al. | |
| 5,916,210 A | 6/1999 | Winston | |
| 5,922,003 A | 7/1999 | Anctil et al. | |
| 5,935,108 A | 8/1999 | Katoh et al. | |
| 5,938,645 A | 8/1999 | Gordon | |
| 5,938,671 A | 8/1999 | Katoh et al. | |
| 5,938,672 A | 8/1999 | Nash | |
| 5,941,869 A | 8/1999 | Patterson et al. | |
| 5,947,985 A | 9/1999 | Imran | |
| 5,948,184 A | 9/1999 | Frantzen et al. | |
| 5,951,480 A | 9/1999 | White et al. | |
| 5,951,482 A | 9/1999 | Winston et al. | |
| 5,954,745 A | 9/1999 | Gertler et al. | |
| 5,968,064 A | 10/1999 | Selmon et al. | |
| 5,972,019 A | 10/1999 | Engelson et al. | |
| 5,985,397 A | 11/1999 | Witt et al. | |
| 5,989,281 A | 11/1999 | Barbut et al. | |
| 5,997,557 A | 12/1999 | Barbut et al. | |
| 6,001,112 A | 12/1999 | Taylor | |
| 6,010,449 A | 1/2000 | Selmon et al. | |
| 6,010,522 A | 1/2000 | Barbut et al. | |
| 6,013,072 A | 1/2000 | Winston et al. | |
| 6,019,778 A | 2/2000 | Wilson et al. | |
| 6,022,362 A | 2/2000 | Lee et al. | |
| 6,027,450 A | 2/2000 | Brown et al. | |
| 6,027,460 A | 2/2000 | Shturman | |
| 6,027,514 A * | 2/2000 | Stine et al. | 606/159 |
| 6,032,673 A | 3/2000 | Savage et al. | |
| 6,036,646 A | 3/2000 | Barthe et al. | |
| 6,036,656 A | 3/2000 | Slater | |
| 6,036,707 A | 3/2000 | Spaulding | |
| 6,039,693 A | 3/2000 | Seward et al. | |
| 6,048,349 A | 4/2000 | Winston et al. | |
| 6,050,949 A | 4/2000 | White et al. | |
| 6,063,093 A | 5/2000 | Winston et al. | |
| 6,066,153 A | 5/2000 | Lev | |
| 6,068,603 A | 5/2000 | Suzuki | |
| 6,068,638 A | 5/2000 | Makower | |
| 6,081,738 A | 6/2000 | Hinohara et al. | |
| RE36,764 E | 7/2000 | Zacca et al. | |
| 6,095,990 A | 8/2000 | Parodi | |
| 6,099,542 A | 8/2000 | Cohn et al. | |
| 6,106,515 A | 8/2000 | Winston et al. | |
| 6,110,121 A | 8/2000 | Lenker | |
| 6,120,515 A * | 9/2000 | Rogers et al. | 606/159 |
| 6,120,516 A | 9/2000 | Selmon et al. | |
| 6,126,649 A | 10/2000 | VanTassel et al. | |
| 6,129,734 A | 10/2000 | Shturman et al. | |
| 6,134,003 A | 10/2000 | Tearney et al. | |
| 6,152,909 A | 11/2000 | Bagaoisan et al. | |
| 6,152,938 A | 11/2000 | Curry | |
| 6,156,046 A * | 12/2000 | Passafaro et al. | 606/159 |
| 6,157,852 A | 12/2000 | Selmon et al. | |
| 6,159,195 A | 12/2000 | Ha et al. | |
| 6,159,225 A | 12/2000 | Makower | |
| 6,165,127 A | 12/2000 | Crowley | |
| 6,179,859 B1 | 1/2001 | Bates et al. | |
| 6,183,432 B1 | 2/2001 | Milo | |
| 6,187,025 B1 | 2/2001 | Machek | |
| 6,190,353 B1 | 2/2001 | Makower et al. | |
| 6,191,862 B1 | 2/2001 | Swanson et al. | |
| 6,193,676 B1 | 2/2001 | Winston et al. | |
| 6,196,963 B1 | 3/2001 | Williams | |
| 6,206,898 B1 | 3/2001 | Honeycutt et al. | |
| 6,217,527 B1 | 4/2001 | Selmon et al. | |
| 6,217,549 B1 | 4/2001 | Selmon et al. | |
| 6,217,595 B1 | 4/2001 | Shturman et al. | |
| 6,221,049 B1 | 4/2001 | Selmon et al. | |
| 6,221,332 B1 | 4/2001 | Thumm et al. | |
| 6,228,049 B1 | 5/2001 | Schroeder et al. | |
| 6,228,076 B1 | 5/2001 | Winston et al. | |
| 6,231,546 B1 | 5/2001 | Milo et al. | |
| 6,231,549 B1 | 5/2001 | Noecker et al. | |
| 6,235,000 B1 | 5/2001 | Milo et al. | |
| 6,238,405 B1 | 5/2001 | Findlay, III et al. | |
| 6,241,667 B1 | 6/2001 | Vetter et al. | |
| 6,241,744 B1 | 6/2001 | Imran et al. | |
| 6,245,012 B1 | 6/2001 | Kleshinski | |
| 6,258,052 B1 | 7/2001 | Milo | |
| 6,263,236 B1 | 7/2001 | Kasinkas et al. | |
| 6,264,611 B1 | 7/2001 | Ishikawa et al. | |
| 6,266,550 B1 | 7/2001 | Selmon et al. | |
| 6,277,138 B1 | 8/2001 | Levinson et al. | |
| 6,283,951 B1 | 9/2001 | Flaherty et al. | |
| 6,283,983 B1 | 9/2001 | Makower et al. | |
| 6,299,622 B1 | 10/2001 | Snow et al. | |
| 6,299,623 B1 | 10/2001 | Wulfman | |
| 6,302,875 B1 | 10/2001 | Makower et al. | |
| 6,305,834 B1 | 10/2001 | Schubert et al. | |
| 6,312,444 B1 | 11/2001 | Barbut | |
| 6,319,242 B1 | 11/2001 | Patterson et al. | |
| 6,319,275 B1 | 11/2001 | Lashinski et al. | |
| 6,330,884 B1 | 12/2001 | Kim | |
| 6,355,005 B1 | 3/2002 | Powell et al. | |
| 6,361,545 B1 | 3/2002 | Macoviak et al. | |
| 6,375,615 B1 | 4/2002 | Flaherty et al. | |
| 6,383,195 B1 | 5/2002 | Richard | |
| 6,383,205 B1 | 5/2002 | Samson et al. | |
| 6,394,976 B1 | 5/2002 | Winston et al. | |
| 6,398,798 B2 | 6/2002 | Selmon et al. | |
| 6,422,736 B1 | 7/2002 | Antonaides et al. | |
| 6,423,081 B1 | 7/2002 | Lee et al. | |
| 6,425,870 B1 | 7/2002 | Flesch | |
| 6,428,551 B1 | 8/2002 | Hall et al. | |
| 6,428,552 B1 | 8/2002 | Sparks | |
| 6,443,966 B1 | 9/2002 | Shiu | |
| 6,445,939 B1 | 9/2002 | Swanson et al. | |
| 6,447,525 B2 | 9/2002 | Follmer et al. | |
| 6,451,036 B1 | 9/2002 | Heitzmann et al. | |
| 6,454,779 B1 | 9/2002 | Taylor | |
| 6,475,226 B1 | 11/2002 | Belef et al. | |
| 6,482,217 B1 | 11/2002 | Pintor et al. | |
| 6,497,711 B1 | 12/2002 | Plaia et al. | |
| 6,501,551 B1 | 12/2002 | Tearney et al. | |
| 6,520,975 B2 | 2/2003 | Branco | |
| RE38,018 E | 3/2003 | Anctil et al. | |
| 6,532,380 B1 | 3/2003 | Close et al. | |
| 6,533,749 B1 | 3/2003 | Mitusina et al. | |
| 6,561,998 B1 | 5/2003 | Roth et al. | |
| 6,565,588 B1 | 5/2003 | Clement et al. | |
| 6,569,177 B1 | 5/2003 | Dillard et al. | |
| 6,592,526 B1 | 7/2003 | Lenker | |
| 6,620,180 B1 | 9/2003 | Bays et al. | |
| 6,623,437 B2 | 9/2003 | Hinchliffe et al. | |
| 6,623,495 B2 | 9/2003 | Findlay, III et al. | |
| 6,623,496 B2 | 9/2003 | Snow et al. | |
| 6,629,953 B1 | 10/2003 | Boyd | |
| 6,638,233 B2 | 10/2003 | Corvi et al. | |
| RE38,335 E | 11/2003 | Aust et al. | |
| 6,652,505 B1 | 11/2003 | Tsugita | |
| 6,652,548 B2 | 11/2003 | Evans et al. | |
| 6,656,195 B2 | 12/2003 | Peters et al. | |

| | | |
|---|---|---|
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065125 A1 | 3/2008 | Olson |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 3732236 C1 | 12/1988 |
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |

| | | | |
|---|---|---|---|
| JP | 2271847 A | 11/1990 | |
| JP | 3186256 A | 8/1991 | |
| JP | 4200459 A | 7/1992 | |
| JP | 5042162 A | 2/1993 | |
| JP | 5056984 A | 3/1993 | |
| JP | 5184679 A | 7/1993 | |
| JP | 6269460 A | 9/1994 | |
| JP | 7075611 B | 8/1995 | |
| SU | 442795 A1 | 9/1974 | |
| SU | 665908 A1 | 6/1979 | |
| WO | WO 8906517 A1 | 7/1989 | |
| WO | WO 92/07500 A2 | 5/1992 | |
| WO | WO 9313716 A1 | 7/1993 | |
| WO | WO 9313717 A1 | 7/1993 | |
| WO | WO 9521576 A1 | 8/1995 | |
| WO | WO 9611648 A1 | 4/1996 | |
| WO | WO 9746164 A1 | 12/1997 | |
| WO | WO 9804199 A1 | 2/1998 | |
| WO | WO 9824372 A1 | 6/1998 | |
| WO | WO 99/39648 A1 | 8/1999 | |
| WO | WO 9952454 A1 | 10/1999 | |
| WO | WO 00/54735 A1 | 9/2000 | |
| WO | WO 00/62913 A1 | 10/2000 | |
| WO | WO 00/68300 A1 | 11/2000 | |
| WO | WO 00/72955 A1 | 12/2000 | |
| WO | WO 01/15609 A1 | 3/2001 | |
| WO | WO 01/19444 A1 | 3/2001 | |
| WO | WO 0130433 A1 | 5/2001 | |
| WO | WO 01/43857 A1 | 6/2001 | |
| WO | WO 0143809 A1 | 6/2001 | |
| WO | WO 02/16017 A2 | 2/2002 | |
| WO | WO 02/45598 A2 | 6/2002 | |

OTHER PUBLICATIONS

Brezinski et al., "Optical Coherence Tomography for Optical Biopsy," Circulation, 93:1206-1213 (1996).
Brezinski et al., "Assessing Atherosclerotic Plaque Morphology: Comparison of Optical Coherence Tomography and High Frequency Intravascular Ultrasound," Heart, 77:397-403 (1997).
Huang et al., "Optical Coherence Tomography," Science, 254:1178-1181 (1991).
International Search Report and Written Opinion of PCT Application No. PCT/US04/12600, dated Jun. 13, 2008, 8 pages total.
International Search Report of PCT Application No. PCT/US04/12601, dated Jun. 30, 2005, 3 pages total.
Mar. 27, 2009 Communication from the European Patent Office regarding corresponding EP Application No. 01 991 343.3 (7 pages).
U.S. Appl. No. 12/431,210, filed Apr. 28, 2009, John B. Simpson et al. (59 pages).
Abstract of JP2206452A (1 page).
Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).
Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).
Translation of Aug. 15, 2007 mailed Japanese Patent Office Action, Application No. 1999-139033.

* cited by examiner

Figure 2
Figure 2A
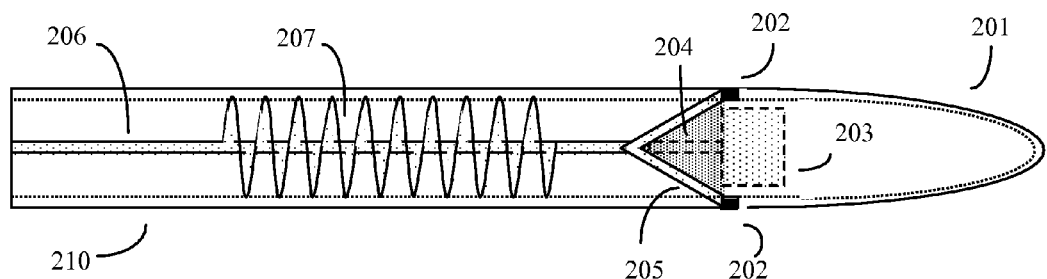
Figure 2B
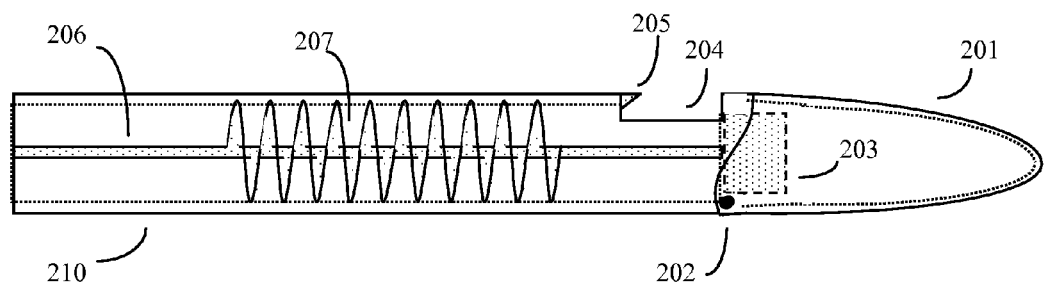
Figure 2C
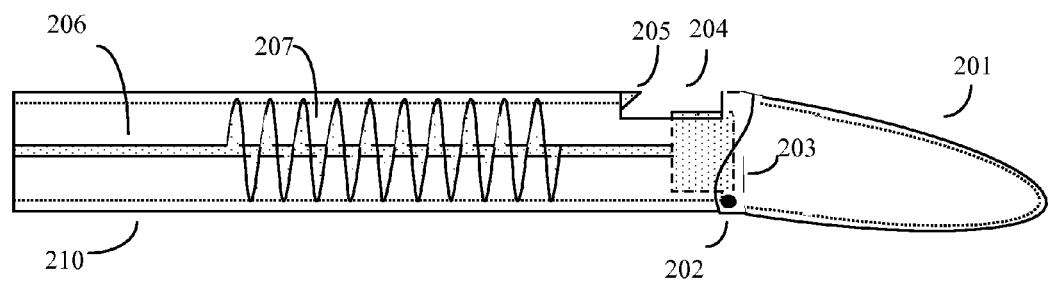

Figure 4
Figure 4A
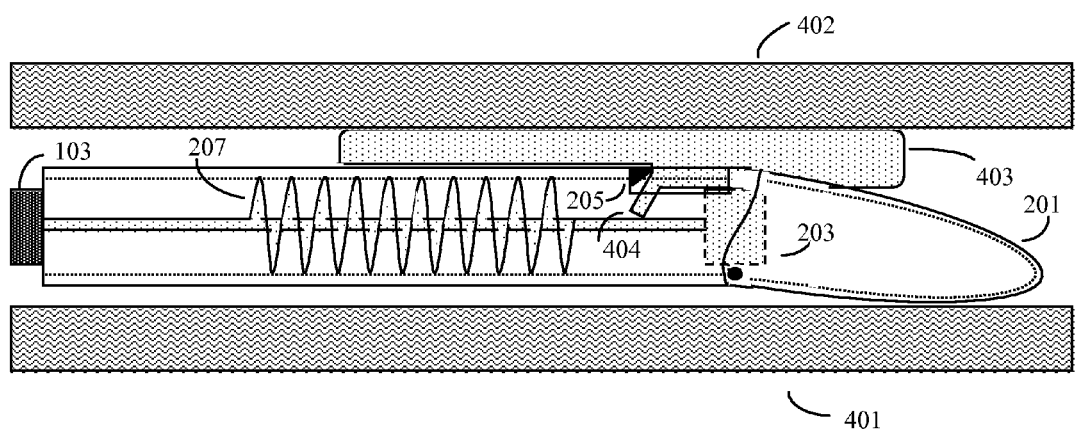
Figure 4B
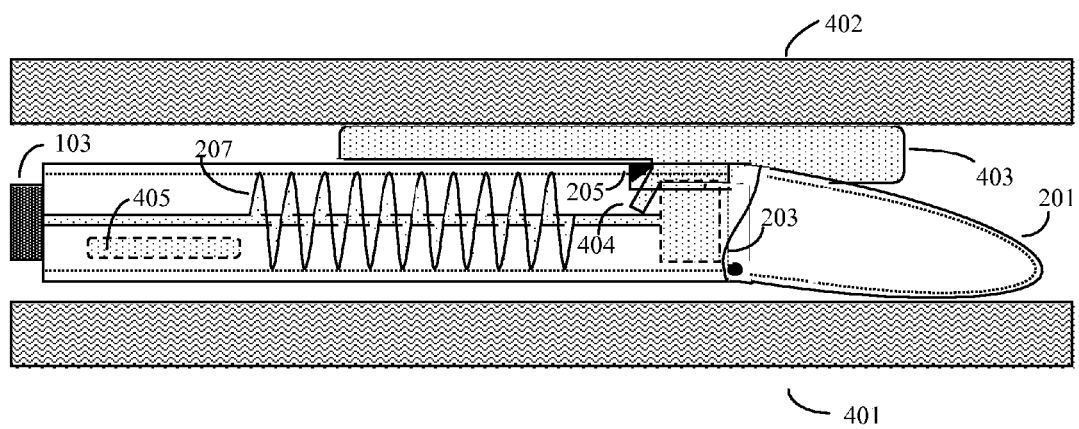

HIGH CAPACITY DEBULKING CATHETER WITH RAZOR EDGE CUTTING WINDOW

BACKGROUND OF THE INVENTION

Restriction of blood circulation due to the atherosclerotic build up of plaque in arteries is the source of much mortality and morbidity. Plaque deposits in cardiac arteries can result in angina and myocardial infarction. Plaque deposits in peripheral arteries of the limbs can result in peripheral artery disease (PAD). PAD affects about 20% of the population over 70, and in more severe forms (which afflict about 2 million people in the U.S.) can lead to non-healing ulcers, infection, and eventually loss of limb due to amputation. Most people die within two years of such amputations.

Although many techniques, such as stenting and balloon angioplasty, have been developed to help restore circulation to plaque occluded cardiac arteries, these methods tend to be less effective for peripheral arteries. Stents, although well suited to low-mobility cardiac arteries, tend to either restenose or frequently break in peripheral limb arteries because these arteries are subjected to greater movement and mechanical stress. Balloon angioplasty, which stretches the artery walls while it compresses and redistributes plaque, tends to cause a greater and typically less acceptable amount of artery wall damage when it is used with peripheral arteries. Additionally, since angioplasty simply redistributes plaque rather than actually removing plaque, in the higher mobility peripheral arteries, the redistributed plaque tends to relatively quickly distribute itself back into an unacceptable configuration again.

From the surgical perspective, one of the most ideal ways to treat arteries blocked by plaque is to remove the plaque from the inside of the artery using an atherectomy catheter. Such catheters, which come in a variety of different designs, can be introduced into the body at a convenient location and threaded inside the artery to the plaque occluded target region (which can usually be determined exactly using fluoroscopy and appropriate radio opaque contrast dyes). Once they are at the correct region, atherectomy catheters then surgically remove the occluding plaque.

Many different types of atherectomy catheter devices have been proposed, including catheters with rotating burrs (Boston Scientific Rotablator), lasers to photo-dissolve tissue (Spectrametics Laser Catheter), and cutter-balloon catheters (Guidant AtheroCath). All have certain drawbacks, however, such as difficulty in traversing through small and torturous arteries to get to the plaque occluded target zone or zones.

One of the biggest problems plaguing prior art atherectomy catheters is the problem of gracefully handing the shaved plaque remnants. Some designs, such as the Rotablator, make no attempt at all to handle the liberated plaque fragments, and instead let the fragments migrate through the circulation. This can cause many problems, because the liberated plaque remnants can be thrombogenic, and can end up causing downstream occlusions. Other catheter designs attempt to reduce this problem by capturing the plaque shavings and safely removing them from the body. Capturing the plaque shavings also makes the samples available for pathologic and medical diagnostic examination, and may give important information as to the root causes behind the plaque build-up in the first place.

Examples of such cutting catheters include Andreas U.S. Pat. No. 5,250,059; Farley, U.S. Pat. No. 5,624,457; Conley U.S. Pat. No. 5,669,920; Schultz U.S. Pat. No. 5,836,957; and Rogers U.S. Pat. No. 6,120,515. Other prior art includes Snow, U.S. application Ser. No. 09/930,372; Methods for removing atheromatous material from a body lumen More recent atherectomy catheters, such as the Fox Hollow SilverHawk articulated rotating blade atherectomy catheter, have been designed to address such issues. The SilverHawk catheter (exemplified by U.S. patent application Ser. Nos. 10/027,418; 10/288,559; 10/896,747; and others) uses a unique rotating blade, window, and hinged hollow nose design, which can be controlled to either assume a straight position or an angled (drooped) position.

To use the SilverHawk atherectomy catheter, the operator will usually first insert a guide wire to the proper location, attach the SilverHawk to the guidewire, and introduce the SilverHawk through a convenient artery port, often located near the groin region. The operator then maneuvers the SilverHawk device to the appropriate region of plaque with the SilverHawk hinged (bendable) nose in a straight configuration. Once at the target zone, the operator then bends the angle of the SilverHawk's hollow nose. The nose contacts the artery wall opposite the plaque target, and which in turn results in an opposing force that presses the catheter's window and cutter against the plaque.

The operator will then spin-up the cutter, and move the catheter across the target zone. The rotary cutter cuts a thin strip of plaque, which is directed, by the motion of the cutter and the device's geometry, into the hollow nose cone. The cuttings stay in the nose cone, where they can eventually be removed from the body and analyzed.

The SilverHawk atherectomy catheter represented a significant advance in the state of the art, because it enabled substantially longer regions (often several centimeters or more) of plaque to be shaved for each pass of the catheter over a region. An additional advantage was that the catheter could be rotated; exposing the window and the rotating blade to another region, and a target region of plaque could thus be shaved multiple times, allowing precise control over the amount and geometry of the plaque reduction process.

Although the SilverHawk catheter demonstrated the utility of this type of approach, further improvements were still desirable. In particular, the available plaque storage space in the device's hollow nose cone was limited, and improvements in trimming partially attached plaque shavings were also desirable.

One problem was that whenever the nose cone filled with plaque, the catheter needed to be pulled from the body, cleaned, and then laboriously rethreaded to the correct location in the target zone again. This tended to significantly prolong the length and effort required for many medical procedures, and thus was undesirable to both physician and patient alike. Methods to reduce this burden were thus highly desirable.

A second problem was how to optimize plaque handling near the edges of trimmed areas. In some cases, plaque would be partially severed by the rotating cutter, yet still remain partially attached to the artery wall. This dangling plaque sometimes had a tendency to deform when a cutter passed over it, rather than be neatly severed and stored in the catheter's plaque storage compartment. Here, an alternative cutting means that could either cut the plaque from the opposite direction, and/or pinch off, cut, and store dangling plaque would be advantageous.

Atherectomy design engineers face some formidable design challenges, however. In order to navigate the narrow and torturous arteries, veins and other lumens of the body, such catheters must have extremely small diameters, usually on the order of 1 to 3 millimeters (3-9 French). At the same time, the devices must be flexible enough to be threaded through such arteries, yet have sections that are rigid enough to accomplish the required positioning, cutting, and plaque storage functions.

Due to these many design constraints, mechanical designs that might be relatively simple to execute with larger diameter devices become very problematic at such extremely small diameters. Additional constraints, such as the need to use biocompatible materials, the need for extremely high reliability, and the need for accommodate a wide variety of different plaque targets in different patients make the design of such devices quite challenging.

BRIEF SUMMARY OF THE INVENTION

The present invention is an improved atherectomy catheter designed with increased plaque carrying cap ability, and an improved ability to trim plaque, including the dangling portions of plaque that are still partially attached to artery or other body lumen walls. The catheter will normally comprise a long catheter tube, with a cutting head attached to the tube comprising at least a hollow rigid tubular portion with a bladed edge window, and an adjustable angle distal nose portion. The catheter head may additionally contain either a moveable plunger or a moveable plunger cutting wheel. The catheter may achieve its plaque cutting action by more than one modality.

In a first cutting modality, an operator controlled variable angle (drooping) nose or nose region is bent by the operator. The tip of the nose contacts an opposite artery wall or other body lumen, forcing (as an equal and opposite reaction) a bladed window opening on the opposite side of the catheter up against a target region of plaque on the opposite artery wall. The operator then retracts a plunger or shield that obscures the bladed edge of the catheter window, and advances the catheter. The bladed window edge shaves the plaque, and plaque shavings pass through the window opening into a hollow storage space inside the catheter, where the shavings are stored. The shavings may then be subsequently removed from the body and subjected to pathological or medical diagnostic analysis as needed.

In a second cutting modality, an operator uses the catheter's moveable plunger to close the catheter's open window. As it closes the window, the plunger presses any dangling plaque that is protruding into the window up against the bladed edge of the window. The dangling plaque is severed by the pinching action of the window blade and the plunger, and again enters the hollow storage space inside the catheter.

In a third cutting modality, an operator spins up a moveable combination plunger and cutting wheel, and uses the spinning plunger/cutting wheel to almost close the catheter's open window, while optionally advancing or retracting the catheter. The dangling plaque is thus subjected to cutting action from both sides, as well as a pinching action, and an optional force due to advancement or retraction of the catheter. The severed plaque fragment and again enters the hollow storage space inside the catheter.

In a fourth cutting modality, an operator may spin up a moveable plunger cutting wheel, and cut plaque by alternately advancing and retracting the catheter head. Plaque will be subjected to cutting from the bladed window when the catheter is advanced, and will be subjected to cutting from the rotating plunger when the catheter is retracted. As before, the shavings will again enter into the hollow storage space inside the catheter.

Normally, when the operator wishes to advance or retract the catheter through the body either towards or away from the target zone, the operator will use a mechanism connected to the plunger to close the window. This helps insure that the bladed window edge will not inadvertently damage non-target regions of the arteries or other body lumens.

It is contemplated that in normal operation, the operator may switch between various cutting modalities as appears best for the given situation. The present design gives the operator a greater number of cutting options than prior art designs, thus allowing quicker and more precise procedures to be accomplished. Due to the fact that the present invention stores the plaque shavings in the relatively large hollow storage space of the catheter body, rather than the relatively small storage space of the catheter nose (as was done with prior art designs), the catheter may additionally operate for a longer period of time before it must be withdrawn from the body for cleaning, and reinserted. This speeds up the procedure time, and reduces the burden on patients and physicians.

In an alternative embodiment of the present invention, sensors may also be added to the design to help the operator properly position the device relative to target plaque or other body lumen targets of interest, and also properly orient the cutting window of the device.

BRIEF DESCRIPTION OF THE DRAWINGS

FIG. 2A shows a top view of the distal catheter cutting head.

FIG. 2B shows a side view of the distal catheter cutting head with the adjustable angle catheter nose in the up configuration.

FIG. 2C shows a side view of the distal catheter cutting head with the nose angled down in a drooped configuration.

FIG. 4A shows the razor edge on the catheter window cutting through plaque with the plug in an open window configuration.

FIG. 4B shows the how dangling plaque may be cut off and stored in the head of the device by closing the plug.

DETAILED DESCRIPTION OF THE INVENTION

The present art is normally intended for use with human patients, as well as various veterinary applications. For simplicity, this combined human or animal use will be referred to as use in mammals, although of course such devices could also be used in appropriate non-mammal animals such as birds, reptiles, and amphibians, etc., as appropriate.

It should also be understood that although the examples of cutting unwanted plaque deposits in arteries are used throughout this disclosure, the actual invention may be used for a broader variety of applications, including removing tumors, getting biopsies, etc. in arteries, veins, and any other tubular or roughly tubular body lumen.

Nomenclature: The handle end of the catheter is the proximal location, and the nose cone tip of the catheter is the distal location.

Figure 1:
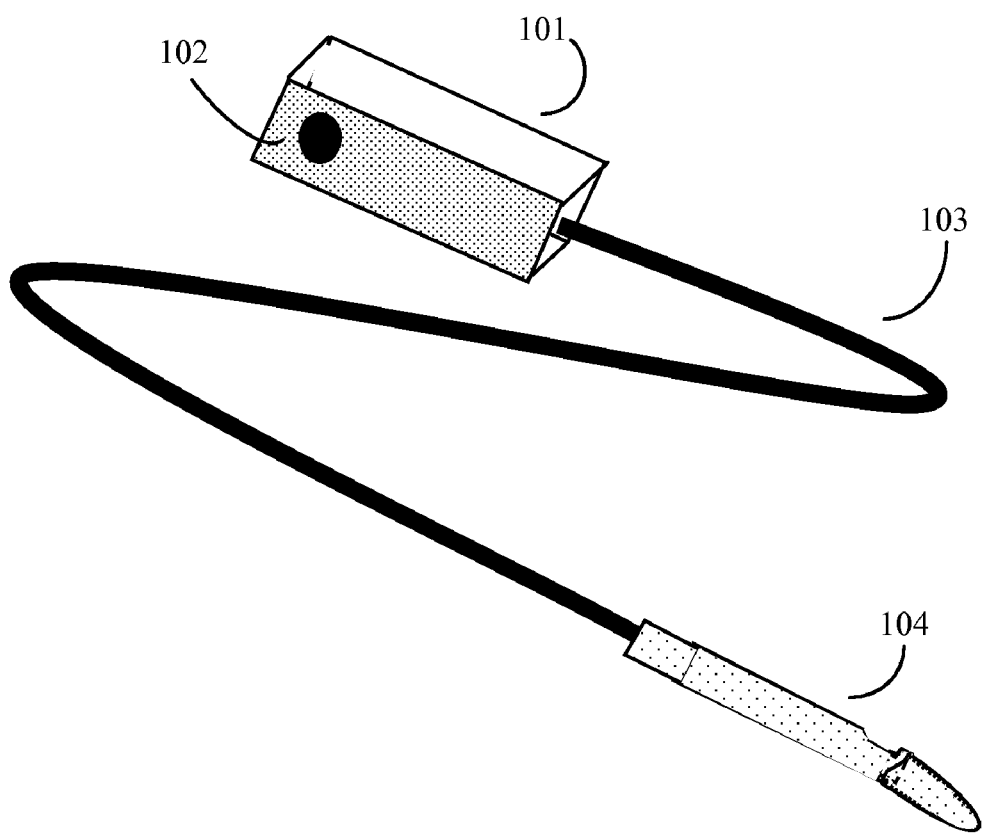
FIG. 1 shows an overall view of the unit, including the proximal operator control, the catheter, and the distal catheter cutting head.

An overview of the device is shown in FIG. 1. The device consists of a handle (101), one or more control knobs, tabs, or switches (102), a long catheter tube or shaft (103), and the cutting atherectomy head (104).

The catheter tube or shaft (103) will typically consist of a flexible tube, which is often hollow and capable of passing a guide wire, as well as optionally other materials such as drugs and contrast materials, control wires, drive shafts, sensors, sensor fibers or wires, ultrasonic signals, and the like. The control wires may optionally be used to operate plunger settings, nose angle, and the like as will be discussed in the next sections.

In some embodiments, the handle (101) may also contain a battery and motor for driving a screw material transport device in the catheter head (104), or a rotating combination plunger and cutter. In this case, the tube (103) may contain a shaft or hollow shaft additionally capable of transmitting torque from a motor mounted in the handle to the atherectomy head.

The cutting atherectomy head (104) will typically consist of a hollow body and a moveable tapered nose, which in some embodiments is connected to the front of the hollow body by at least one hinge. The head will additionally consist of at least a window with a razor edge, and a moveable plunger or combination plunger/cutter that can transition from a more distal (open window) position to a more proximal (closed window) position. Head (104) may additionally contain openings or ports to accommodate a guidewire to allow the catheter head to be precisely threaded through torturous arteries, veins, or other body lumens.

In the event that use with a guide wire is desired, to allow the head's bladed window and plunger cutting mechanism to operate freely and without risk accidentally cutting or entangling with the guide wire, the guide wire may be routed to exit from the proximal region of the catheter head, and then reenter the catheter head at the distal region of the head, thus skipping the plaque cutting and storage regions of the head. In some configurations, the guide wire will reenter the catheter head at the distal nose region, travel through the nose end of the head for a short distance, and then finally exit the head again through a third exit port, often located near the tip of the catheter's nose located at the extreme distal end of the catheter.

FIG. 2A, 2B, and 2C show close-ups of the cutting atherectomy head (104) from various angles. FIG. 2A shows the head from the top. The figure shows the head's adjustable angle nose cone (201), hinge pins (202), moveable plug (203), window opening (204), window blade edge (205), the plug movement shaft (206) an optional helical screw to help move and compact any plaque shavings (207), and the main body of the head (210).

The catheter's nose (201) usually has a tapered or conical atraumatic design intended to allow the catheter head to easily migrate through arteries. It may be composed of softer materials, and may additionally have an internal coiled spring or other means to allow the tip to bend somewhat as needed to migrate through torturous arteries and other body lumen structures.

FIG. 2B shows the same head from the side. Here the adjustable angle nose (201) is shown in the "up" or straight configuration, which allows the catheter head to migrate though the torturous arteries and body lumens with maximum ease. In this figure the plug (203) is shown in the extended configuration and the window (204) is open. In actual operation however, when the head is being moved through the arteries to a target site, plug (203) will normally be in a closed position, closing window (204), and normally blocking window blade (205). This closed position helps to prevent the window blade (205) from accidentally nicking or cutting non-target regions of the arteries or other body lumens while the device is being moved to and from its various target zones.

FIG. 2C shows the head from the side, showing the catheter operating in a cutting configuration after the catheter head has been threaded to its designated target zone. Once the catheter is in position, the adjustable angle catheter nose (201) is put into a bent or drooped position through either a cam mechanism (not shown), or other means. Suitable cam mechanisms and deflection means for adjusting the angle of similar type catheter noses were previously taught by copending application Ser. Nos. 10/896,741, and 10/027,418, the contents of which are incorporated herein by reference.

In this angled or drooped position, the nose cone (201), which is shown held to the main body (210) by hinge pins (202), rotates to a "bent" configuration. This adjustable angle nose is typically rotated by the operator increasing the angle of the bend until the nose tip makes contact with the opposite wall of a body lumen (i.e. an opposite artery wall). Once the nose tip makes contact with an opposite wall, an equal and opposite force is generated (by the normal laws of physics) that acts to push or "urge" window (204) and the blade (205) against the target zone on the opposite lumen wall. This target is usually a plaque occluded region of an artery wall.

This design thus differs from earlier cutting catheter designs, such as the Guidant AtheroCath, which used a balloon on one side of the cutting head to force the cutting portion of the catheter against the target plaque.

One problem with earlier cutting catheter designs is the catheters either did not collect the plaque shavings at all (potentially causing significant complications and adverse effects), or else the earlier designs had only a relatively limited ability (storage volume) to store this collected plaque.

As an example, prior art atherectomy catheters typically stored plaque shavings in the hollow distal (nose) side of the catheter head. Although functional, the volume of this hollow nose is quite limited. As an unfortunate consequence, medical procedures had to be frequently interrupted whenever the catheter head filled up with plaque. The catheter then had to be carefully withdrawn, stored plaque removed, then slowly and carefully reinserted back to the target zone. This prolonged the medical procedures, and led to strain on the patient and physician, as well as encouraging less complete plaque removal.

By contrast, the present art solves this limited storage problem by adapting a novel design in which the plaque cutting blade (205) is mounted on one or more edges of a hollow window (204) that in turn opens up into a much larger plaque shaving storage area (206) contained in the main body of the catheter head (210).

A second advantage of the present invention's bladed window design that it gives the operator a wider variety of cutting options. The operator may use the bladed window (204, 205) as a scraper, paring off unwanted plaque by advancing the catheter. The operator may use the bladed window, in combination with a plunger (203) to pinch off plaque. The operator may use the bladed window with a combination plunger and rotary cutter to cut plaque from both directions. The net effect is that the operator has a greater variety of cutting means at his or her disposal, and can thus choose the most appropriate means to fit the particular target at hand.

In some embodiments, the catheter may additionally have sensors, such as directional ultrasonic or infrared sensors, mounted on the catheter head. In one embodiment, the orientation of the sensor or sensors is directed to give the operator information as to the status of the plaque and/or artery of or other body lumen that is facing the cutting window of the catheter. This can allow the operator to determine if the catheter is in the proper orientation relative to its intended target. Examples of such sensors were described in more detail in application Ser. No. 10/421,980, the contents of which are incorporated herein by reference.

Device dimensions: Typically the catheter cutting head (210) will have a diameter between about 1 to 2.2 millimeters. The cutting window (204) will typically have a length of about 1.2 to 2.5 millimeters. In embodiments where the plunger (203) is a plunger equipped with a cutting wheel that contains a cam or other orientation control mechanism that allows the cutting wheel portion of the plunger to extend slightly outside the window, the plunger orientation control mechanism may allow the plunger to at least temporarily be locked into a position that allows the cutting outer edge of the plunger to extend about 0.025 to 0.64 mm outside the cutting window.

This adjustable "slightly outside" configuration can also be used when the plunger does not have a cutting edge as well, as a slightly protruding plunger creates a "safety razor" type configuration in which any tendency of the blade to cut too deeply is mitigated by the force of the artery wall against the protruding plunger.

The net effect of the present design is to allow the operator to move the catheter backward along the target region of plaque, and shave off a long thin portion of this plaque using the cutting edge of plunger (203). The operator may then move the catheter forward, and cut off plaque using blade (205). In this configuration, both forward and backward movement can produce cutting activity, if desired.

The plunger (203) will typically have a diameter of about 1.14 mm, and a width typically at least as long as window (204). The window facing side of the plunger and may have a dull edge, a sharp cutting edge, other edge. The geometry of the plunger's window-facing edge may be chosen so that when the plunger is moved to close the window, window blade (205) may be partially or totally covered or obscured by the plunger. Alternatively, the plunger may be designed to provide a flat or curved edge to help pinch material, and may be designed as to stop just short of contacting the window blade so as to avoid dulling window blade (205). If plunger (203) is designed to function as a cutting wheel, then usually some sort of safety stop will be used so as to prevent plunger (203) from coming into total contact with blade edge (205).

If the plunger is designed to additionally operate as a rotating cutting wheel, then the catheter will have a mechanism to rotate the plunger/cutting wheel at high speeds, typically greater than 100 rotations per minute (rpm), preferably around 8000 rotations per minute (rpm).

As previously discussed, in some configurations, the plunger will be mounted on a shuttle or cam mechanism to allow the operator to adjust the protrusion of the plunger from the window. This will allow plunger (203) to function somewhat as the stop on a safety razor, and help prevent blade (205) from accidentally penetrating too far into plaque during a cutting step. That is, plunger (203) may be angled as to protrude partially outside of the window (204), and in particular further outside window (204) than blade (205). Thus if blade (205) starts to cut too deep, the protruding portion of plunger (203) will then start to generate a downward deflection force to help prevent blade (205) from cutting at a larger depth.

The cutting edge of the blades may be optionally hardened by an appropriate coating, such as ME-92, tungsten carbide, or other suitable materials as taught by U.S. Pat. Nos. 4,771, 774; 5,242,460; 5,312,425; 5,431,673; and 5,674,232.

In other cases, the action of blade can be facilitated by ultrasonic vibration, laser cutting, radiofrequency electrodes, and the like. In this case, appropriate mechanisms (i.e. a piezoelectric ultrasonic vibrator, laser diode or optical fiber, electrodes, etc. may also be provided in the catheter head to drive the blade as needed. If the action of the ultrasonic, laser, or electrode cutter is sufficiently robust enough as to make it a spinning blade unnecessary, then the blade may either not be spun up, or the blade rotary mechanism may be omitted, or a non-rotating blade may be used.

In many embodiments, it will be useful to allow the location and orientation of the catheter head to be identified by constructing the catheter head (210), nose (201), and cutting window/plunger region (204), (203) out of suitable combinations of translucent and radio opaque materials, thus, for example, enabling the region distal to the cutting window to be distinguished from the region proximal to the cutting head by fluoroscopy or other X-ray detection means.

In addition to fluoroscopy localization, other modalities, such as light (optical) and sonic (ultrasonic) localization methods may also be used. Here orientation may be facilitated by running a fiber optic strand through the catheter tube (103) (not shown) to an appropriate location on the catheter head, and determining the location and orientation of the head by optical means. Alternatively an ultrasonic transducer or pickup may be incorporated into the catheter head.

Typically the flexible outer catheter tube (103) between the handle (101) and the head (104) will have a length between 50 cm and 200 cm, a diameter between 1 French (0.33 mm) and 12 French (4 mm), and will usually be between 3 French (1 mm) and 9 French (3 mm) in diameter. The catheter body will often be made from extruded organic polymers such as polyvinylchloride, polyurethane, polyester, polytetrafluoroethylene (PTFE), silicon rubber, or similar materials. The catheter body may be reinforced as needed with wires, coils, or filaments as needed to give the body additional strength and to control rigidity and pushabiliy.

Portions of the catheter head (104) (distal region of the catheter) will often be rigid or partially rigid, and can be made from materials such as metals, hard plastics, composite materials, NiTi steel (optionally coated with titanium nitride, tantalum, ME-92® or diamonds. Usually stainless steel or platinum/iridium will be used. The length of the middle portion of the catheter head may vary between about 5 to 35 mm, and will usually be between about 10 to 25 mm; however alternative lengths (longer or shorter) may also be used.

As previously discussed, the extreme distal end of the catheter head (the nose) (201) will usually be made to be both flexible and atraumatic so as to allow the catheter to be threaded through arteries with maximum ease and minimum trauma. Because, in this design, the nose is no longer used to store plaque, this nose design may be optimized to accommodate the plunger, optional cams or drive mechanisms, and also optimized to allow easy passage of the catheter through arteries. In some cases, the distal tip will have an inner coil construction to maximize flexibility. The distance between the rigid part of the catheter head and the distal end tip of the flexible catheter nose will typically be between 10 and 30 mm, but may vary as needs dictate.

The present device will often be designed to make use of a monorail guidewire to assist in positioning the cutter to the proper location at the target site. Usually the guidewire will have diameters between about 0.010" and 0.032", usually around 0.014". Although this guidewire may optionally pass through much of the 50 to 200 cm length of the flexible catheter through a hollow hole in the center of the catheter, it will usually be desirable to have the guidewire leave catheter head proximal to the plaque storage, window, cutting and cutting driver mechanism, and then rejoin the catheter head after these portions have been passed. This prevents interference with the plaque debulking mechanism. Thus the guidewire may have a portion that is external to the catheter head in this region.

In some embodiments, it may be desirable to protect the portion or portions of the guidewire that is briefly external to the catheter head by a guidewire lumen or a telescoping guidewire lumen with a length between about 2 and 14 cm, or even longer as needed to accommodate higher plaque storage volumes. This telescoping guidewire lumen protects both the guidewire from accidental cutting or entanglement with the blade and window, and also helps protect the patient's artery or other body lumen linings from inadvertent excessive pressure while the catheter head traverses narrow passages.

Figure 3:
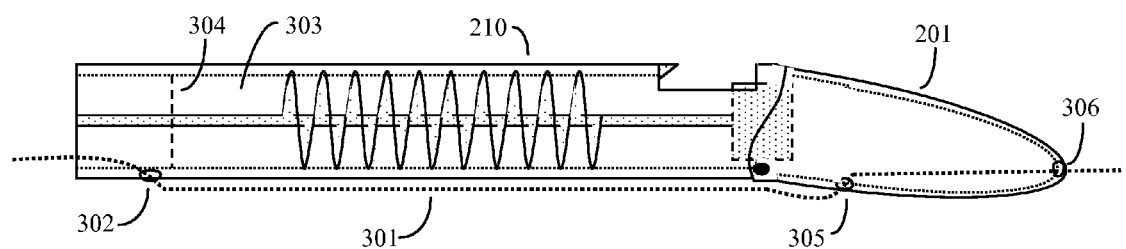
FIG. 3 shows how a guide wire may be threaded through the catheter and the distal cutting head.

FIG. 3 shows one example of how the catheter of the present invention may interact with a guide wire. In order to do this, either the catheter tube (103) and or the catheter head and nose (210), (201) may have hollow passages or openings in order to be compatible with such guide wires. This is shown in FIG. 3. Here a guide wire (301) originally threaded through the hollow catheter tube (103) exits the catheter head (210) at aperture (302). The guide wire thus bypasses the hollow plaque storage region of the catheter head (303) which in this example may be separated from the hollow catheter tube (103) by a divider (304).

In this embodiment, the guidewire travels outside of the head of the catheter (210) for a while (e.g. 5 to 15 cm) until it reaches a first opening (305) in the catheter nose. The guide wire may then be threaded through the catheter nose until it reaches a second opening (306), where it may then exit. Other guide wire configurations may be used, or alternatively, no guide wire at all may be used.

As shown in FIG. 4A, once the catheter head has been maneuvered to the appropriate target zone, the adjustable angle nose (201) is angled or drooped, and the plug (203) is pushed distally (201), opening up window (204) and exposing the window knife edge (205). The angled or drooped nose (201) contacts the opposite wall of artery or body lumen (401), providing pressure to force or "urge" window (204) and knife edge (205) against the wall of the artery (402) and against the target plaque (403). The operator can then advance (more) the catheter head (210) forward (distally) by applying forward pressure to the catheter tube (103) or advancing some other type of drive mechanism.

Blade (205) shaves off some of this plaque (403) and this removed plaque (404) enters the hollow cavity of catheter head (210). Helical screw (207) can then act to move this plaque further back into the storage cavity. As previously discussed, plunger (203) can optionally be rotated by a cam mechanism and advanced partially out of the window (205) in order to provide greater control over the depth of the cut by blade (205).

As shown in FIG. 4B, the dangling plaque (404) can also be trimmed by moving plunger (203) proximally back into the catheter head (210) thus closing or partially closing window (204). The plunger forces the dangling plaque (404) up against the knife edge (205) pinching or cutting the dangling plaque. This severed plaque (405) then enters the hollow capillary head where it can be moved to the back by an optional helical screw (207), suction, or other mechanism.

As previously discussed, in alternative embodiments, plunger (203) may be a rotating plunger that also has its own cutting head along the edge of the plunger facing the window. Alternatively plunger (203) may have an edge configuration designed to shield or partially shield blade (205) from inadvertent contact with body lumens when the window (204) is closed or partially closed by the plunger (203). The plunger mechanism may additionally have various cams or stops designed to place the plunger at the appropriate angle and orientation necessary to perform its function.

Figure 5:
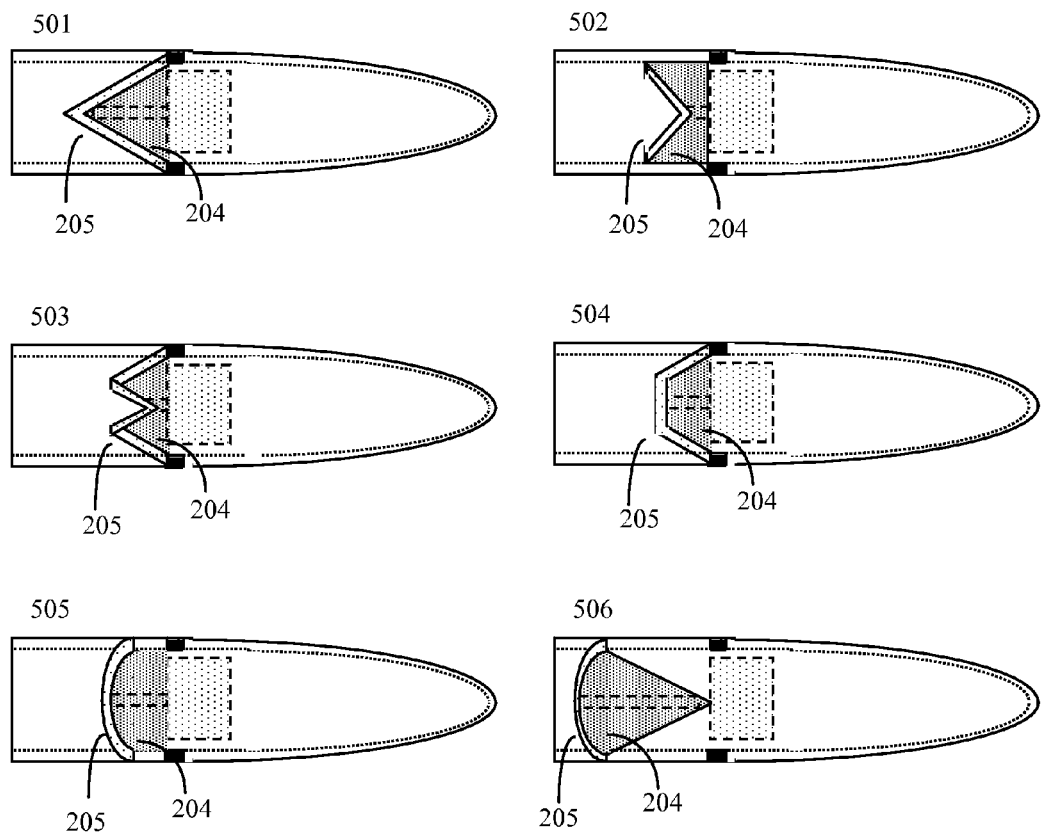
FIG. 5 shows a variety of different catheter window blade edges.

FIG. 5 (501) to (506) shows various alternate blade (205) and window (204) configurations that may be used with the device.

The invention claimed is:

1. A catheter comprising:
a flexible tube comprising a proximal end and a distal end;
said flexible tube having dimensions and flexibility compatible with migration through at least some arteries or veins or other body lumens of a living mammal;
a catheter head with dimensions also compatible with migration through at least some arteries or veins or other body lumens of a living mammal;
said catheter head comprising a substantially rigid housing coupled to the distal end of said flexible tube;
said rigid housing comprising at least a window to the space outside said housing that also opens into a hollow inner portion of said housing;
at least one edge of said window comprising a blade with at least one cutting edge facing in the distal direction of said catheter;
a moveable plunger disposed in the hollow portion of said rigid housing, the moveable plunger comprising a plug and a rotatable shaft having a helical screw that moves shaved material proximally upon rotation of the shaft;
wherein said catheter contains a mechanism to allow an operator of said catheter to adjust said plunger to open or close said window;
wherein said plunger can be powered to rotate; and
wherein said plug has a cutting edge along the circumference of the plug that faces in the proximal direction of said catheter.

2. The catheter of claim 1, wherein said catheter additionally contains a deflectable nose region mounted on the distal end of said rigid housing, and a mechanism to allow said operator to deflect said nose region against a body lumen, thereby pushing said window and said blade against an opposite wall of said body lumen, allowing said blade to cut material from said body lumen.

3. The catheter of claim 1, wherein said plug has a cylindrical configuration; wherein the axis of said cylindrical plug is substantially aligned along the long axis of said catheter; and wherein said plunger can be powered to rotate at a speed greater than 100 rpm.

4. The catheter of claim 1, in which said window is bounded on all sides by said rigid housing.

5. The catheter of claim 1, wherein said plunger is configured to allow said window blade to contact a body lumen when said plunger has opened said window; and wherein the geometry of said window and said hollow portion is configured to allow material shaved by said blade to enter into the hollow portion of said housing when the position of said catheter head is manipulated by said operator.

6. The catheter of claim 1, wherein said hollow portion of said rigid housing is used to store material excised from a body lumen.

7. The catheter of claim 1, in which the proximal end of said catheter tube is connected to a handle or control mechanism for controlling said catheter, said handle or control mechanism being designed for use by a human operator, and said handle or control mechanism remaining outside the body of said mammal at all times.

8. The catheter of claim 1, in which said flexible tube is hollow, and said flexible tube acts to conduct torque, drugs, contrast dyes, ultrasonic vibration, fiber optical signals, mechanical deflection signals, electrical current, electrical signals, or a guide wire across some or all of the length of the tube.

9. The catheter of claim 1, in which said catheter head comprises a sensor oriented to survey material that is positioned near the blade zone of said window and in which said sensor is selected from the group consisting of ultrasound transducer arrays, optical fibers, and coherence tomography devices.

10. The catheter of claim 1, wherein the plug is able to be disposed distal to said window.

11. A catheter comprising:
a flexible tube comprising a proximal end and a distal end;
said flexible tube having dimensions and flexibility compatible with migration through at least some arteries or veins or other body lumens of a living mammal;
a catheter head with dimensions also compatible with migration through at least some arteries or veins or other body lumens of a living mammal;
said catheter head comprising a substantially rigid housing coupled to the distal end of said flexible tube;
said rigid housing comprising at least a window to the space outside said housing that also opens into a hollow inner portion of said housing;
at least one edge of said window comprising a blade with at least one cutting edge facing in the distal direction of said catheter;
a moveable plunger disposed in the hollow portion of said rigid housing, the moveable plunger comprising a plug and a rotatable shaft having a helical screw that moves shaved material proximally upon rotation of the shaft;
wherein said moveable plunger can be manipulated by an operator of said catheter to open or close said window;

wherein said catheter additionally contains a deflectable nose region mounted on the distal end of said rigid housing, and a mechanism to allow said operator to deflect said nose region against a body lumen, thereby pushing said window and said blade against an opposite wall of said body lumen, allowing said blade to cut material from said body lumen;

wherein said plunger can be powered to rotate; and wherein said plug has a cutting edge along the circumference of the plug that faces in the proximal direction of said catheter.

12. The catheter of claim 11, wherein said plunger is configured to allow said window blade to contact a body lumen when said plunger has opened said window; and wherein the geometry of said window and said hollow portion is configured to allow material shaved by said blade to enter into the hollow portion of said housing when the position of said catheter head is manipulated by said operator.

13. The catheter of claim 11, wherein said hollow portion of said rigid housing is used to store material excised from a body lumen.

14. The catheter of claim 11, in which the proximal end of said catheter tube is connected to a handle or control mechanism for controlling said catheter, said handle or control mechanism being intended for use by a human operator, and said handle or control mechanism remaining outside the body of said mammal at all times.

15. The catheter of claim 11, in which said flexible tube is hollow, and said flexible tube acts to conduct torque, drugs, contrast dyes, ultrasonic vibration, fiber optical signals, mechanical deflection signals, electrical current, electrical signals, or a guide wire across some or all of the length of the tube.

16. The catheter of claim 11, wherein said plug has a cylindrical configuration; wherein the axis of said cylindrical plug is substantially aligned along the long axis of said catheter; and wherein said plunger can be powered to rotate at a speed greater than 100 rpm.

17. The catheter of claim 11, in which said window is bounded on all sides by said rigid housing.

18. The catheter of claim 11, wherein the plug is able to be disposed distal to said window.

19. A catheter comprising:
a flexible tube comprising a proximal end and a distal end;
said flexible tube having dimensions and flexibility compatible with migration through at least some arteries or veins or other body lumens of a living mammal;
a catheter head with dimensions also compatible with migration through at least some arteries or veins or other body lumens of a living mammal;
said catheter head comprising a substantially rigid housing coupled to the distal end of said flexible tube;
in which said catheter head comprises a sensor oriented to survey material that is positioned near the blade zone of said window;
said rigid housing additionally comprising at least a window to the space outside said housing that also opens into a hollow inner portion of said housing;
at least one edge of said window comprising a blade with at least one cutting edge facing in the distal direction of said catheter;
a moveable plunger disposed in the hollow portion of said rigid housing, the moveable plunger comprising a plug and a rotatable shaft having a helical screw that moves shaved material proximally upon rotation of the shaft;
wherein said moveable plunger can be manipulated by an operator of said catheter to open or close said window;
wherein said catheter additionally contains a deflectable nose region mounted on the distal end of said rigid housing, and a mechanism to allow said operator to deflect said nose region against a body lumen, thereby pushing said window and said blade against an opposite wall of said body lumen, allowing said blade to cut material from said body lumen;
wherein said plunger can be powered to rotate; and
wherein said plug has a cutting edge along the circumference of the plug that faces in the proximal direction of said catheter.

20. The catheter of claim 19, wherein said plunger is configured to allow said window blade to contact a body lumen when said plunger has opened said window; and wherein the geometry of said window and said hollow portion is configured to allow material shaved by said blade to enter into the hollow portion of said housing when the position of said catheter head is manipulated by said operator.

21. The catheter of claim 19, wherein said hollow portion of said rigid housing is used to store material excised from a body lumen.

22. The catheter of claim 19, in which the proximal end of said catheter tube is connected to a handle or control mechanism for controlling said catheter, said handle or control mechanism being intended for use by a human operator, and said handle or control mechanism remaining outside the body of said mammal at all times.

23. The catheter of claim 19, in which said flexible tube is hollow, and said flexible tube acts to conduct torque, drugs, contrast dyes, ultrasonic vibration, fiber optical signals, mechanical deflection signals, electrical current, electrical signals, or a guide wire across some or all of the length of the tube.

24. The catheter of claim 19, in which said sensor is selected from the group consisting of ultrasound transducer arrays, optical sensors, optical fibers, and coherence tomography devices.

25. The catheter of claim 19, wherein said plug has a cylindrical configuration; wherein the axis of said cylindrical plug is substantially aligned along the long axis of said catheter; and wherein said plunger can be powered to rotate at a speed greater than 100 rpm.

26. The catheter of claim 19, in which said window is bounded on all sides by said rigid housing.

27. The catheter of claim 19, wherein the plug is able to be disposed distal to said window.

* * * * *